(12) United States Patent
Schleicher et al.

(10) Patent No.: US 8,855,769 B2
(45) Date of Patent: *Oct. 7, 2014

(54) CONNECTOR ASSEMBLIES FOR IMPLANTABLE STIMULATORS

(71) Applicant: Boston Scientific Neuromodulation Corporation, Valencia, CA (US)

(72) Inventors: Brett Schleicher, Valencia, CA (US); Rafael Carbunaru, Valley Village, CA (US); Todd K. Whitehurst, Frederick, MD (US); Kristen N. Jaax, Santa Clarita, CA (US); Greg Baldwin, Golden, CO (US); Andrew DiGiore, San Francisco, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/172,559

(22) Filed: Feb. 4, 2014

(65) Prior Publication Data

US 2014/0155957 A1    Jun. 5, 2014

Related U.S. Application Data

(63) Continuation of application No. 13/735,994, filed on Jan. 7, 2013, now Pat. No. 8,682,438, which is a continuation of application No. 12/262,789, filed on Oct. 31, 2008, now Pat. No. 8,352,035.

(60) Provisional application No. 60/984,259, filed on Oct. 31, 2007.

(51) Int. Cl.
*A61N 1/00* (2006.01)
*A61N 1/372* (2006.01)
*A61N 1/378* (2006.01)

(52) U.S. Cl.
CPC ........ *A61N 1/37205* (2013.01); *A61N 1/37235* (2013.01); *A61N 1/3787* (2013.01)
USPC .................................. 607/37; 607/36; 607/2

(58) Field of Classification Search
USPC .................................................. 607/2, 36–37
See application file for complete search history.

(56) References Cited

U.S. PATENT DOCUMENTS 5,193,539 A    3/1993 Schulman et al.
5,193,540 A    3/1993 Schulman et al.

(Continued)

FOREIGN PATENT DOCUMENTS

WO    WO-02068048 A1    9/2002
WO    WO-03039649 A2    5/2003
WO    WO-2004047919 A2    6/2004

OTHER PUBLICATIONS

U.S. Appl. No. 12/262,789, Official Communication mailed Sep. 22, 2011.

(Continued)

*Primary Examiner* — Nicole F Lavert
(74) *Attorney, Agent, or Firm* — Lowe Graham Jones PLLC; Bruce E. Black (57) ABSTRACT

Exemplary systems include a stimulator configured to be implanted within a patient, the stimulator having a body defined by at least one side surface disposed in between distal and proximal end surfaces, and a connector assembly configured to be coupled to the stimulator and extend parallel to the at least one side surface of the stimulator. The connector assembly is further configured to facilitate removable coupling of a lead having one or more electrodes disposed thereon to the stimulator.

20 Claims, 12 Drawing Sheets

(56) References Cited

U.S. PATENT DOCUMENTS

| | | |
|---|---|---|
| 5,312,439 A | 5/1994 | Loeb |
| 5,350,407 A | 9/1994 | McClure et al. |
| 6,051,017 A | 4/2000 | Loeb et al. |
| 6,164,284 A | 12/2000 | Schulman et al. |
| 6,185,452 B1 | 2/2001 | Schulman et al. |
| 6,208,894 B1 | 3/2001 | Schulman et al. |
| 2002/0107546 A1 | 8/2002 | Ostroff et al. |
| 2004/0098054 A1 | 5/2004 | Eckerdal et al. |
| 2004/0215280 A1 | 10/2004 | Dublin et al. |
| 2005/0055056 A1 | 3/2005 | Olson |
| 2009/0112272 A1 | 4/2009 | Schleicher et al. |

OTHER PUBLICATIONS

U.S. Appl. No. 12/262,789, Official Communication mailed Feb. 28, 2012.

U.S. Appl. No. 13/735,994 Official Communication mailed Aug. 7, 2013.

CONNECTOR ASSEMBLIES FOR IMPLANTABLE STIMULATORS

RELATED APPLICATIONS

The present application is a continuation of U.S. patent application Ser. No. 13/735,994 filed Jan. 7, 2013, now allowed, which is a continuation of U.S. patent application Ser. No. 12/262,789 filed Oct. 31, 2008, now U.S. Pat. No. 8,352,035, which claims priority under 35 U.S.C. §119(e) to U.S. Provisional Patent Application No. 60/984,259 filed Oct. 31, 2007, all of which are hereby incorporated by reference in their entirety.

BACKGROUND

A wide variety of medical conditions and disorders have been successfully treated using an implantable stimulator. Implantable stimulators typically stimulate tissue, such as a nerve, by generating and outputting an electrical stimulation current according to programmed stimulation parameters.

One type of implantable stimulator is known as a microstimulator. Microstimulators are typically characterized by a small, cylindrical housing containing electronic circuitry that produces the desired electric stimulation current between spaced electrodes. These stimulators are implanted proximate to the target tissue so that the stimulation current produced by the electrodes stimulates the target tissue to reduce symptoms or otherwise provide therapy for a wide variety of conditions and disorders.

Another type of implantable stimulator is known as an implantable pulse generator (IPG). A typical IPG includes a multi-channel pulse generator housed in a rounded titanium case. The IPG is generally coupled to a lead with a number of electrodes disposed thereon. Stimulation current is generated by the IPG and delivered to target tissue via the electrodes on the lead.

As will be readily appreciated, a key part of patient treatment using an implanted stimulator is the proper placement of the stimulator such that the electrodes coupled thereto are proximate to the stimulation site to be stimulated. If the electrodes are optimally placed near the stimulation site, stimulation can be realized over a wide range of parameters and power consumption can be minimized. However, optimal placement of a stimulator within a patient is often difficult to accomplish.

SUMMARY

Exemplary systems include a stimulator configured to be implanted within a patient, the stimulator having a body defined by at least one side surface disposed in between distal and proximal end surfaces, and a connector assembly configured to be coupled to the stimulator and extend parallel to the at least one side surface of the stimulator. The connector assembly is further configured to facilitate removable coupling of a lead having one or more electrodes disposed thereon to the stimulator.

Exemplary stimulation assemblies include a stimulator configured to be implanted within a patient, the stimulator having a body defined by at least one side surface disposed in between distal and proximal end surfaces, a connector assembly configured to be coupled to the stimulator and extend parallel to the at least one side surface of the stimulator, and an encasing configured to at least partially surround the stimulator and the connector assembly. The connector assembly is further configured to facilitate removable coupling of a lead having one or more electrodes disposed thereon to the stimulator.

Exemplary methods include providing a stimulator coupled to a connector assembly, removably coupling a lead having one or more electrodes disposed thereon to the connector assembly, generating electrical stimulation with the stimulator, and applying the electrical stimulation to one or more stimulation sites within a patient via the one or more electrodes. In some examples, the stimulator has a body defined by at least one side surface disposed in between distal and proximal end surfaces and the connector assembly is configured to extend parallel to the at least one side surface of the stimulator.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

5A-5D are top views of a stimulator and each illustrate alternative configurations for coupling the conductive wires to electrical circuitry within the stimulator according to principles described herein.

DETAILED DESCRIPTION

Systems and methods for coupling one or more leads to an implantable stimulator are described herein. In some examples, a stimulator having a body defined by at least one side surface disposed in between distal and proximal end surfaces is provided. In some examples, one or more connector assemblies may be coupled to and extend parallel to the at least one side surface of the stimulator. Each connector assembly is configured to receive a lead having at least one electrode disposed thereon. Each lead may be selectably removed from the one or more connector assemblies. In this manner, different types of leads may be electrically coupled to the stimulator in order to facilitate different electrical stimulation therapies for a patient.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

As used herein and in the appended claims, the term "stimulator" will be used broadly to refer to any type of device that is configured to be implanted within a patient to deliver electrical stimulation to a stimulation site within the patient. The term "stimulation site" refers to any nerve, muscle, organ, or other tissue within a patient that is stimulated by an implantable stimulator.

Figure 1:
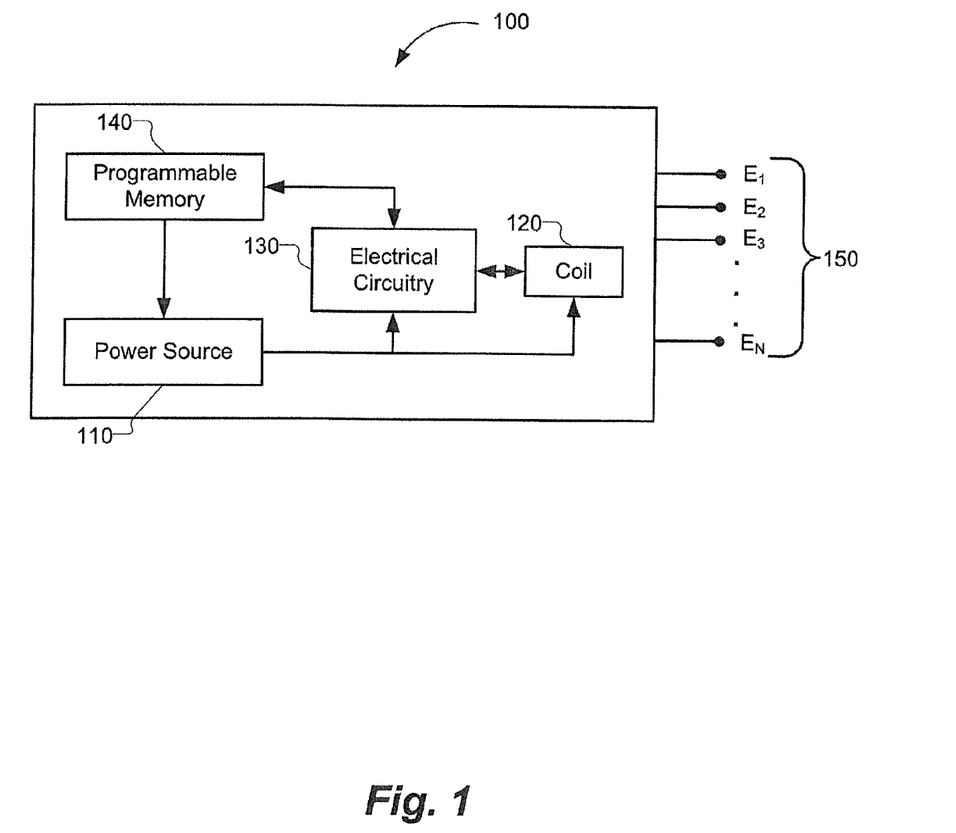
FIG. 1 illustrates an exemplary stimulator that may be used to apply electrical stimulation to a stimulation site within a patient according to principles described herein.

To facilitate an understanding of the systems and methods described herein, a more detailed description of an implantable stimulator and its operation will now be given. FIG. 1 illustrates an exemplary stimulator 100 that may be used to apply electrical stimulation to a stimulation site within a patient. Various details associated with the manufacture, operation, and use of implantable stimulators are disclosed in U.S. Pat. Nos. 5,193,539; 5,193,540; 5,312,439; 6,185,452; 6,164,284; 6,208,894; and 6,051,017. All of these listed patents are incorporated herein by reference in their respective entireties.

As illustrated in FIG. 1, the stimulator 100 includes a number of components. It will be recognized that the stimulator 100 may include additional and/or alternative components as may serve a particular application.

A power source 110 is configured to output voltage used to supply the various components within the stimulator 100 with power and/or to generate the power used for electrical stimulation. The power source 110 may include a primary battery, a rechargeable battery (e.g., a lithium-ion battery), a super capacitor, a nuclear battery, a mechanical resonator, an infrared collector (receiving, e.g., infrared energy through the skin), a thermally-powered energy source (where, e.g., memory-shaped alloys exposed to a minimal temperature difference generate power), a flexural powered energy source (where a flexible section subject to flexural forces is part of the stimulator), a bioenergy power source (where a chemical reaction provides an energy source), a fuel cell, a bioelectrical cell (where two or more electrodes use tissue-generated potentials and currents to capture energy and convert it to useable power), or the like.

The stimulator 100 may also include a coil 120 configured to receive and/or emit a magnetic field (also referred to as a radio frequency (RF) field) that is used to communicate with, or receive power from, one or more external devices. Such communication and/or power transfer may include, but is not limited to, transcutaneously receiving data from the external device, transmitting data to the external device, and/or receiving power used to recharge the power source 110.

The stimulator 100 may also include electrical circuitry 130 configured to generate the electrical stimulation current that is delivered to the stimulation site via one or more electrodes 150 coupled to the stimulator 100. For example, the electrical circuitry 130 may include one or more processors, capacitors, integrated circuits, resistors, coils, and/or any other component configured to generate electrical stimulation current.

The stimulator 100 may also include a programmable memory unit 140 configured to store one or more stimulation parameters. The programmable memory unit 140 allows a patient, clinician, or other user of the stimulator 100 to adjust the stimulation parameters such that the stimulation applied by the stimulator 100 is safe and effective in treating a particular patient. The programmable memory unit 140 may include any type of memory unit such as, but not limited to, random access memory (RAM), static RAM (SRAM), a hard drive, or the like.

The stimulation parameters may control various parameters of the stimulation current applied to damaged neural tissue including, but not limited to, the frequency, pulse width, amplitude, waveform, electrode configuration (i.e., anode-cathode assignment), burst pattern (e.g., continuous or intermittent), duty cycle or burst repeat interval, ramp on time, and ramp off time.

Specific stimulation parameters may have different effects on different damaged neural tissue within a patient. Thus, in some examples, the stimulation parameters may be adjusted or modified as may serve the particular patient being treated.

As shown in FIG. 1, the stimulator 100 may be coupled to a number of electrodes 150 configured to apply the electrical stimulation current to the stimulation site. The electrodes 150 will also be referred to herein as "electrode contacts." As shown in FIG. 1, there may be any number of electrodes 150 coupled to the stimulator 100 as may serve a particular application. In some examples, one or more of the electrodes 150 may be designated as stimulating electrodes and one of the electrodes 150 may be designated as an indifferent electrode used to complete one or more stimulation circuits. In some embodiments, as will be described in more detail below, the electrodes 150 may be disposed on the outer surface of the stimulator 100. Additionally or alternatively, the electrodes 150 may be disposed on one or more leads that are electrically coupled to the stimulator 100.

Figure 2:
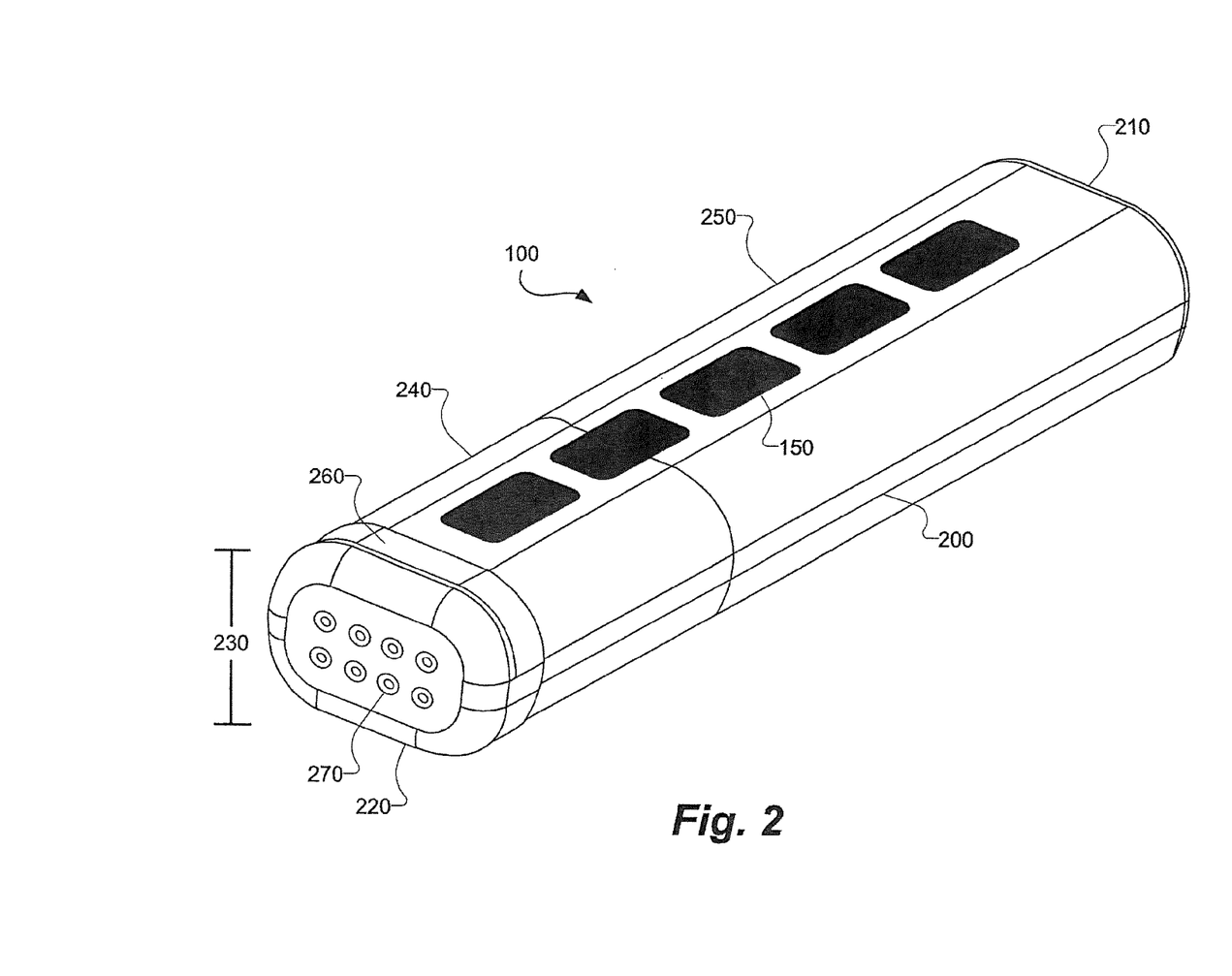
FIG. 2 illustrates an exemplary structure of an implantable stimulator according to principles described herein.

FIG. 2 illustrates an exemplary structure of the implantable stimulator 100. In some embodiments, as shown in FIG. 2, a body of the stimulator 100 may be defined by at least one side surface 200 disposed in between a distal end surface 210 and a proximal end surface 220. The at least one side surface 200 may include any number of surfaces as may serve a particular application.

To illustrate, the stimulator 100 shown in FIG. 2 has a generally rectangular cross-section with corner rounding. The rectangular cross-section shape of the stimulator 100 allows the stimulator 100 to be implanted within a patient in a predetermined orientation. In addition, the slightly significant aspect ratio (cross-section) of the stimulator 100 minimizes the profile, or height 230, of the stimulator 100, which reduces implantation discomfort and skin erosion in many patients. The minimized height 230 also improves the aesthetic appeal of the stimulator 100 when implanted. It will be recognized, however, that the rectangular shape of the stimulator 100 shown in FIG. 2 is merely exemplary of the many different dimensional configurations of the stimulator 100. For example, the stimulator 100 may have a cylindrical shape, a long oval shape, or any other suitable shape as may serve a particular application.

As shown in FIG. 2, the stimulator 100 may include multiple assemblies. For example, the stimulator 100 may include a first assembly 240 coupled to a second assembly 250. Each assembly may be configured to house different components of the stimulator 100.

In some examples, the first assembly 240 houses the coil 120, the electrical circuitry 130, the programmable memory 140, and/or any other component of the stimulator 100 as may serve a particular application. The first assembly 240 may be made out of any suitable material that allows the coil 120 to emit and receive a magnetic field used to communicate with an external device or with another implanted device. For example, the first assembly 240 may be made out of a ceramic material, glass, plastic, a polymer, a metal (e.g., Titanium) configured to allow the passage of a magnetic field, or any other suitable material. Because the first assembly 240 is sometimes made out of a ceramic material, it is sometimes referred to as a ceramic window.

The second assembly 250 shown in FIG. 2 may be configured to house the power source 110. Because the second assembly 250 is typically longer than the first assembly 240, the second assembly 250 is often referred to as the main body of the stimulator 100. In some examples, the second assembly 250 is made out of a conductive metal (e.g., Titanium). Additionally or alternatively, the second assembly 250 may be made out of ceramic, glass, or any other suitable material.

In some examples, the stimulator 100 may also include a header assembly 260 at either end of the stimulator body. The header assembly 260 may be made out of any suitable material such as, but not limited to, a ceramic material, glass, plastic, a polymer, or a metal (e.g., Titanium). As shown in FIG. 2, the header assembly 260 may include one or more feedthroughs 270 configured to facilitate passage therethrough of one or more conductive paths (e.g., wires, vias, etc.) from the electrical circuitry 130 disposed within the stimulator 100 to one or more devices or assemblies located outside the stimulator 100.

For illustrative purposes only, it will be assumed in the examples given herein that the stimulator 100 includes a first assembly 240, a second assembly 250, and a header assembly 260, as described in connection with FIG. 2. However, it will be recognized that the stimulator 100 may include any number of assemblies made out of any combination of materials. For example, the stimulator 100 may only include a single assembly that houses all the components of the stimulator 100. Alternatively, the stimulator 100 may include more than two assemblies. In general, the external surface of the stimulator 100 may be made out of glass, ceramic, plastic, polymers, metal, metal-alloys, or any other suitable material.

It is often desirable for the stimulator 100 to be coupled to multiple electrodes 150 to facilitate more precise electrical stimulation of a stimulation site within a patient. Multiple electrodes 150 also allow physicians to account for variations in patient anatomy, provide an increased range of stimulation, accommodate or recover from stimulator migration, and provide an increased number of treatment options.

Hence, in some examples, a plurality of electrode 150 may be disposed on the outer surface of the stimulator 100. While this type of configuration is effective in some applications, the number of treatable areas of the body are restricted due to the thickness of the stimulator 100. Moreover, if one or more of the electrodes 150 becomes defective, the entire stimulator 100 may have to be replaced, which is taxing on the patient.

To this end, the stimulator 100 may additionally or alternatively be configured to be removably coupled to one or more leads with a plurality of electrodes 150 disposed thereon. In this manner, different leads having different capabilities may be selectively coupled to the stimulator 100 in order to facilitate a desired stimulation therapy for a patient.

Figure 3:
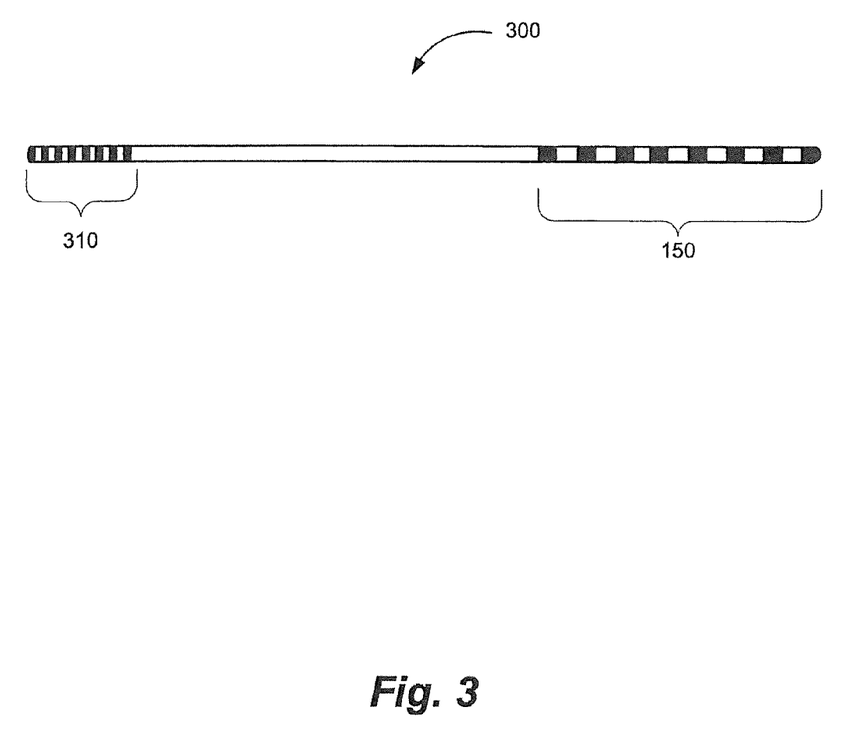
FIG. 3 is a side view of an exemplary lead having a plurality of electrodes disposed thereon according to principles described herein.

FIG. 3 is a side view of an exemplary lead 300 having a plurality of electrodes 150 disposed thereon. In some examples, the lead 300 is substantially cylindrical. However, it will be recognized that the lead 300 may have any suitable shape as may serve a particular application.

As shown in FIG. 3, the lead 300 may include a plurality of electrodes 150 disposed on a distal portion thereof. The number of electrodes 150 may vary as may serve a particular application. For illustrative purposes only, FIG. 3 shows that there are eight electrodes 150 disposed on the distal portion of the lead 300.

In some examples, the lead 300 may also include a plurality of electrical contacts 310 disposed on a proximal portion thereof. Each electrical contact 310 is electrically coupled to one of the electrodes 150 via one or more conductive wires, vias, or other paths within the lead 300. As will be described in more detail below, the proximal portion of the lead 300 having the electrical contacts 310 is configured to be inserted into a connector assembly that is a part of or coupled to the stimulator 100. In this manner, the lead 300 may be removably coupled to the stimulator 100. Contacts 150 and 310 may be made out of any suitable conductive material as may serve a particular application.

As mentioned, the stimulator 100 may include or be coupled to one or more connector assemblies configured to facilitate electrical coupling of the lead 300 to the stimulator 100. As will be described in more detail below, the connector assemblies may be configured to facilitate electrical coupling of one or more leads 300 to the stimulator 100.

Figure 4:
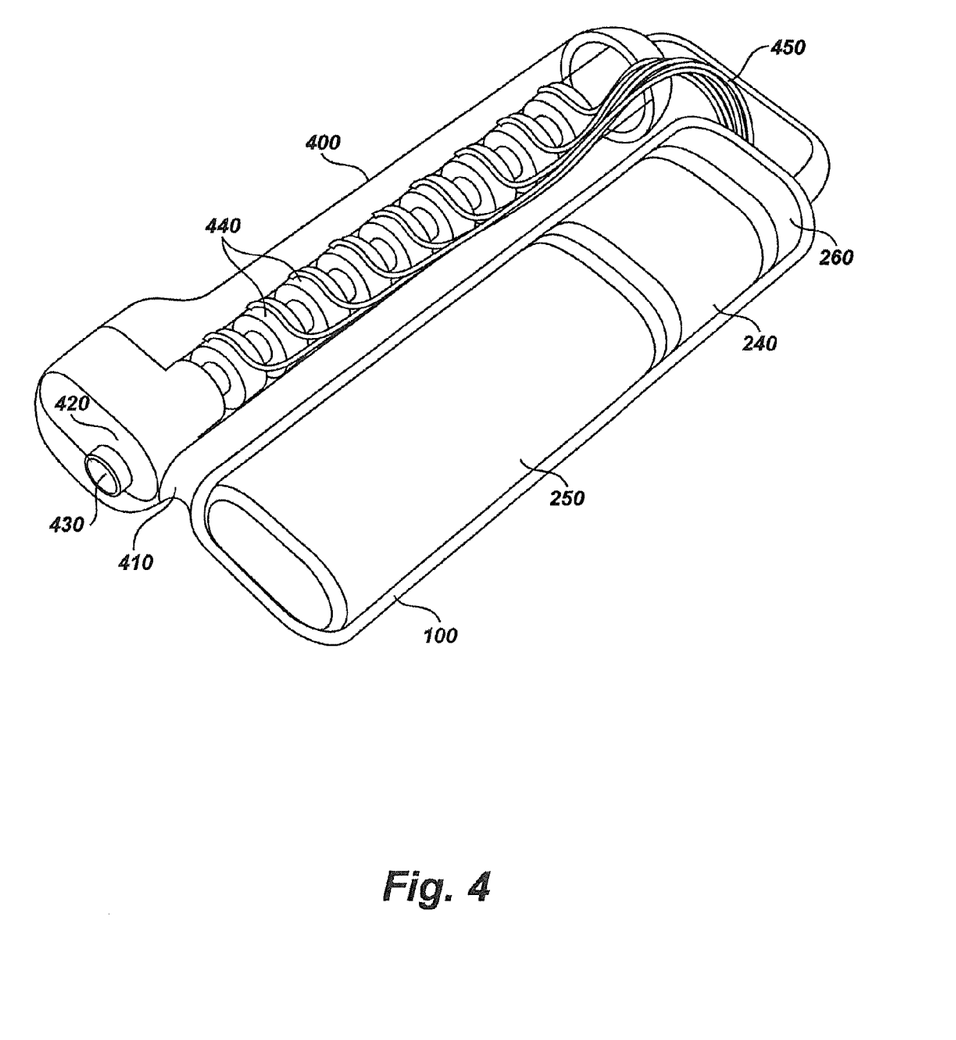
FIG. 4 is a wireframe perspective view of a stimulator coupled to a connector assembly according to principles described herein.

FIG. 4 is a wireframe perspective view of a stimulator 100 coupled to a connector assembly 400. As shown in FIG. 4, the connector assembly 400 may be coupled to one of the sides of the stimulator 100 such that the length of the connector assembly 400 is substantially collinear with the length of the stimulator 100.

In some examples, as shown in FIG. 4, the length of the connector assembly 400 may be substantially equal to the length of the stimulator 100. Alternatively, the length of the connector assembly 400 may be any other size in relation to the length of the stimulator 100 as may serve a particular application.

In some examples, the connector assembly 400 may be coupled to the stimulator 100 using any suitable epoxy, metal bond, or other coupling means. Additionally, or alternatively, the connector assembly 400 may be coupled to the stimulator 100 with a polymer or other material as may serve a particular application. In some examples, the material used to couple the connector assembly 400 to the stimulator 100 is flexible. Additionally or alternatively, one or more circuits, traces, and/or wires used to couple the connector assembly 400 to the stimulator 100 may be flexible. In this manner, the stimulator 100 may flex to conform to various locations within the patient.

Additionally, or alternatively, as shown in FIG. 4, an encasing 410 made out of any suitable flexible or rigid material (e.g., a polymer, silicone, or metal) may be placed at least partially around the stimulator 100 and connector assembly 400. The encasing 410 may be configured to reinforce the connection between the connector assembly 400 and the stimulator 100. Alternatively, the encasing 410 may be the only means for coupling the connector assembly 400 to the stimulator 100. A flexible material may allow the device to be placed in various locations in the body, flex to conform to anatomy, and increase patient comfort. A rigid material may yield a more robust system. A material with a balance between flexibility and structural integrity may also be used as may serve a particular application.

As mentioned, in some examples, the encasing 410 may be made out of silicone. One or more sutures may be tied around the silicone encasing 410 to affix the stimulator 100 and connector assembly 400 to an implant location within a patient. When the sutures are tied around the silicone encasing 410, the indentation of the silicone caused by the sutures may stabilize the stimulator 100 and connector assembly 400 and minimize migration. The external silicone layer may also serve as a protection and a seal configured to prevent harmful biological agents from entering the stimulator 100 and/or connector assembly 400.

As shown in FIG. 4, the connector assembly 400 may include a hollow lumen 420 extending at least partially therethrough and in communication with an opening 430. In some examples, the opening 430 may be disposed at either end of the connector assembly 400. The opening 430 and the lumen 420 are configured to receive the proximal portion of the lead 300, as will be described in more detail below.

A plurality of spaced ring contacts 440 may be in communication with (e.g., disposed within) the lumen 420 of the connector assembly 400. Each ring contact 440 may be configured to make electrical contact with one of the corresponding electrical contacts 310 disposed on the proximal portion of the lead 300 when the lead 300 is inserted into the lumen 420. While ring contacts 440 are shown in FIG. 4, it will be recognized that the ring contacts 440 may be of any suitable shape or size. Moreover, it will be recognized that the ring contacts 440 may include any electrical contact made out of any suitable conductive material.

As shown in FIG. 4, each ring contact 440 may be coupled to electrical circuitry within the stimulator 100 by means of a plurality of conductive wires 450. Wires 450 may include any conductive conduit including, but not limited to, physical wires, metal traces, circuits, and vias that may be used to electrically couple the ring contacts 440 to the electrical circuitry 130 disposed within the stimulator 100. Moreover, it will be recognized that the wires 450 may be flexible.

The conductive wires 450 may be coupled to electrical circuitry 130 disposed within the stimulator 100 in any of a number of different ways. For example, FIGS. 5A-5D are top views of the stimulator 100 and each illustrate alternative configurations for coupling the conductive wires 450 to electrical circuitry 130 disposed within the stimulator 100.

Figure 5A:
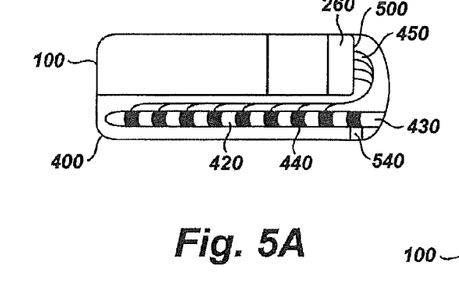
Figure 5B:
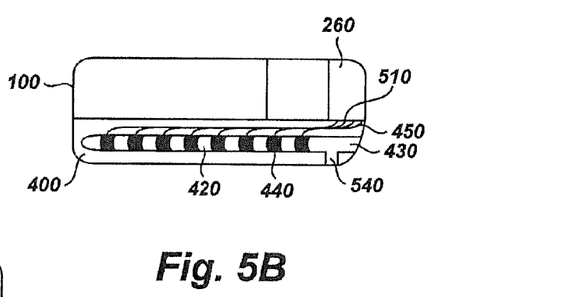
Figure 5C:
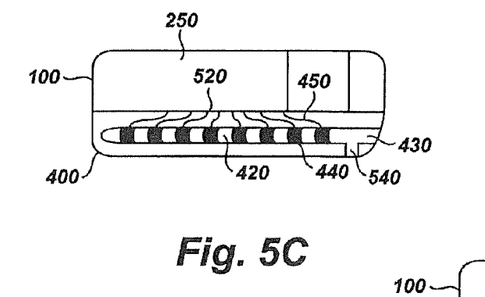
Figure 5D:
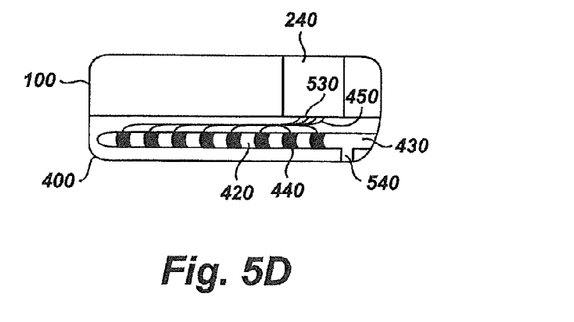

For example, as shown in FIG. 5A, the wires 450 may be routed from the ring contacts 440 to the electrical circuitry 130 via one or more feedthroughs (not shown) located at a top surface 500 of the header assembly 260. FIG. 5B illustrates an alternative configuration wherein the wires 450 are routed from the ring contacts 440 to the electrical circuitry 130 via one or more feedthroughs (not shown) located at a side surface 510 of the header assembly 260. FIG. 5C illustrates an alternative configuration wherein the wires 450 are routed from the ring contacts 440 to the electrical circuitry 130 via one or more feedthroughs (not shown) located at a side surface 520 of the second assembly 250. FIG. 5D illustrates an alternative configuration wherein the wires 450 are routed from the ring contacts 440 to the electrical circuitry 130 via one or more feedthroughs (not shown) located at a side surface 530 of the first assembly 240.

In some examples, any suitable device or mechanism may be used to secure a lead 300 within the connector assembly 400 after the lead 300 has been inserted therein. For example, FIGS. 5A-5D each show a set screw receptacle 540 disposed within the connector assembly 400. In some examples, after the lead 300 has been inserted into the connector assembly 400, a set screw may be disposed within the set screw receptacle 540 and tightened in order to apply retaining force to the lead 300. Additionally or alternatively, any number of snaps, retention rings, clips, adhesives, cams, retention springs, keyways, and quarter turns may be used to retain the lead 300 within the connector assembly 400.

Figure 6A:
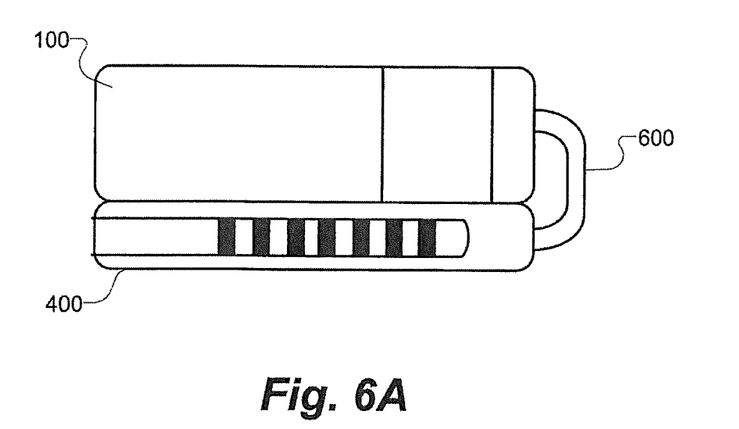
FIG. 6A shows a configuration wherein the wires that couple the ring contacts to the electrical circuitry within the stimulator are encased in a flexible or rigid boot according to principles described herein.
Figure 6B:
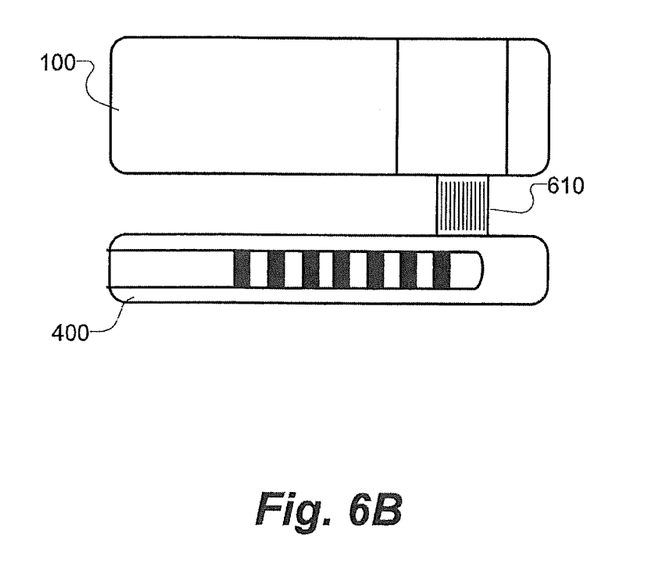
FIG. 6B shows the wires encased in a ribbon cable according to principles described herein.

FIG. 6A is a top view of the stimulator 100 and connector assembly 400 and shows that the wires 450 that couple the ring contacts 440 to the electrical circuitry 130 disposed within the stimulator 100 may be encased in a flexible or rigid boot 600. The boot 600 may be configured to protect the wires 450 from an external environment and/or from breaking and may be made out of any suitable material as may serve a particular application including, but not limited to, a polymer, silicone, metal, rubber, plastic, etc. FIG. 6B illustrates an alternative configuration wherein a ribbon cable 610 is configured to protect the wires 450. The ribbon cable 610 may be flexible or rigid as may serve a particular application. It will be recognized that any additional or alternative means for protecting the wires 450 may be used.

In some examples, the stimulator 100 may include multiple connector assemblies 400 to facilitate the coupling of two or more leads 300 to the stimulator 100. In this manner, an increased number of stimulation electrodes may be used to apply electrical stimulation to one or more stimulation sites within a patient.

Figure 7:
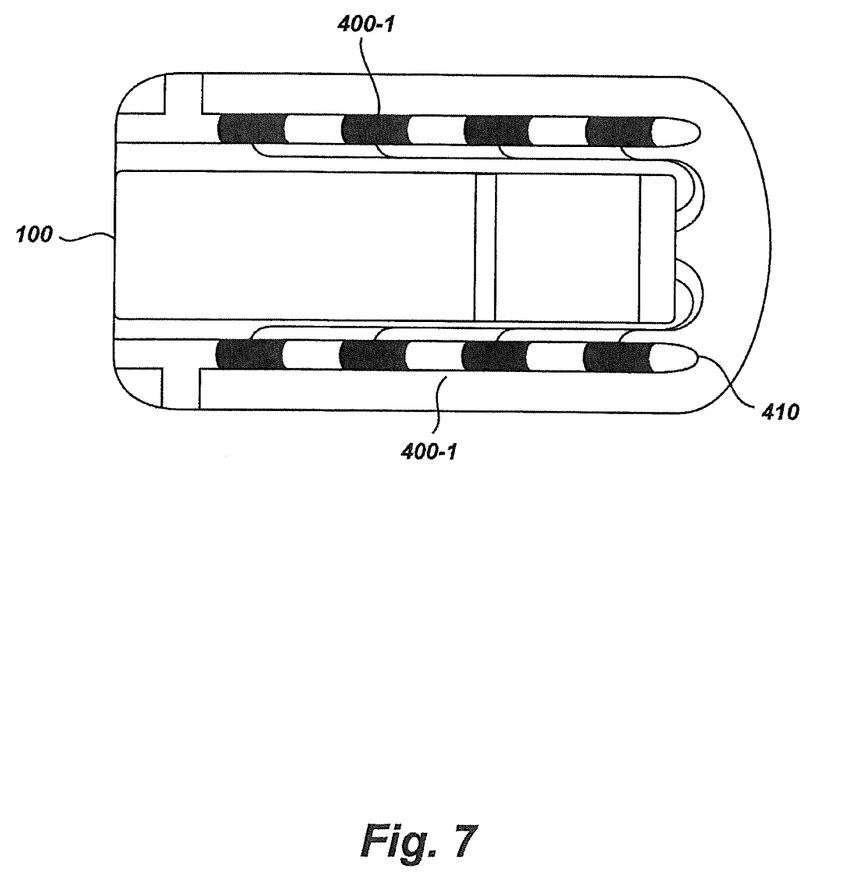
FIG. 7 is a top view of a stimulator having two connector assemblies coupled thereto according to principles described herein.

To illustrate, FIG. 7 is a top view of a stimulator 100 having two connector assemblies 400-1 and 400-2 coupled thereto. Connector assemblies 400-1 and 400-2 will be referred to collectively herein as "connector assemblies 400". Each connector assembly 400 may be configured to receive a corresponding lead 300. It will be recognized that any number of connector assemblies 400 may be coupled to the stimulator 100.

Figure 8A:
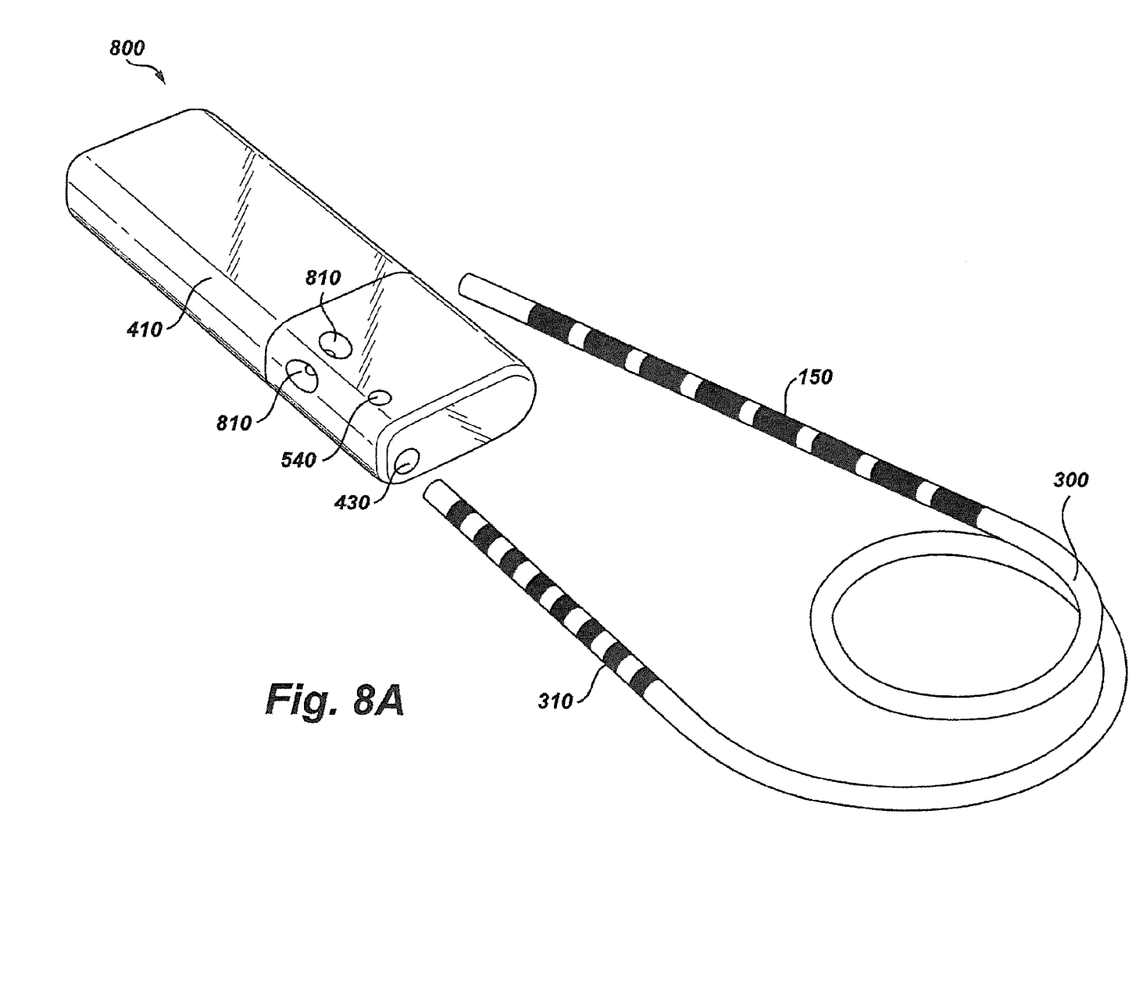
FIG. 8A is a perspective view of an encased stimulator with a connector assembly coupled to one of its sides according to principles described herein.
Figure 8B:
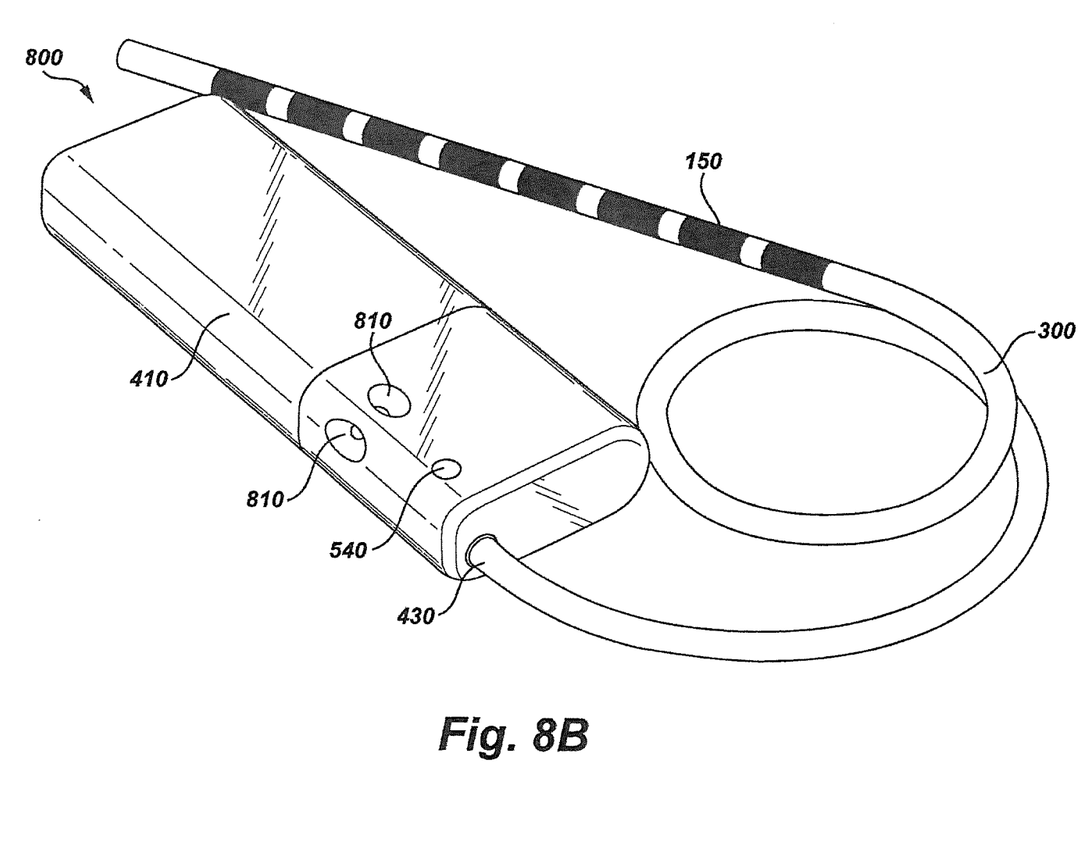
FIG. 8B shows the lead after it has been inserted into the connector assembly of FIG. 8A according to principles described herein.

FIG. 8A is a perspective view of stimulation assembly 800 that includes a stimulator 100 (not shown) and a connector assembly 400 (not shown) encased within an encasing 410. FIG. 8A also shows a lead 300 prior to being inserted into the opening 420 of the connector 430 and into the connector assembly 400. As shown in FIGS. 8A-8B, one or more suturing holes 810 may be included within the encasing 410. A channel may run between the holes 810. In this manner, a physician may thread one or more sutures 180 or other anchoring devices to anchor the stimulation assembly 800 to fascia or any other suitable location within the patient. Also shown in FIGS. 8A-8B is the set screw receptacle 540 into which a set screw may be inserted to affix the lead 300 to the connector assembly 400.

In some examples, a plurality of stimulators 100 and their corresponding connector assemblies 400 may be coupled together to facilitate an increased number of electrodes 150 through which electrical stimulation may be applied to one or more stimulation sites.

Figure 9A:
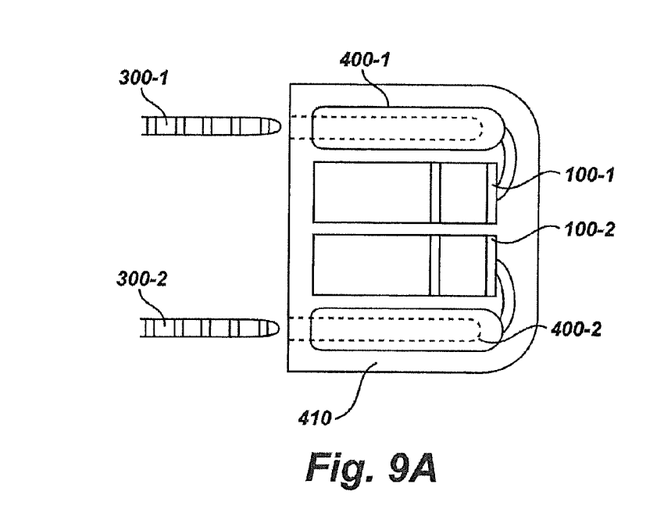
FIG. 9A illustrates an exemplary configuration where first and second stimulators and their corresponding connector assemblies are coupled one to another according to principles described herein.
Figure 9B:
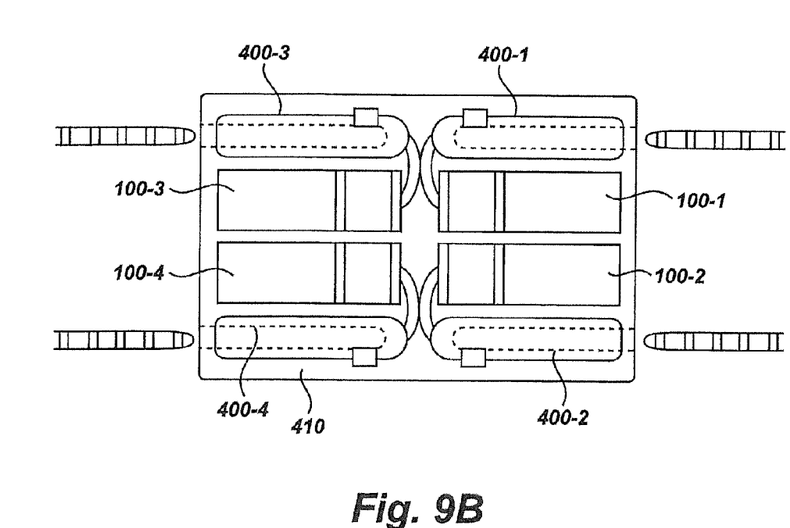
FIG. 9B shows four stimulators and their respective connector assemblies coupled together within an encasing according to principles described herein.
Figure 9C:
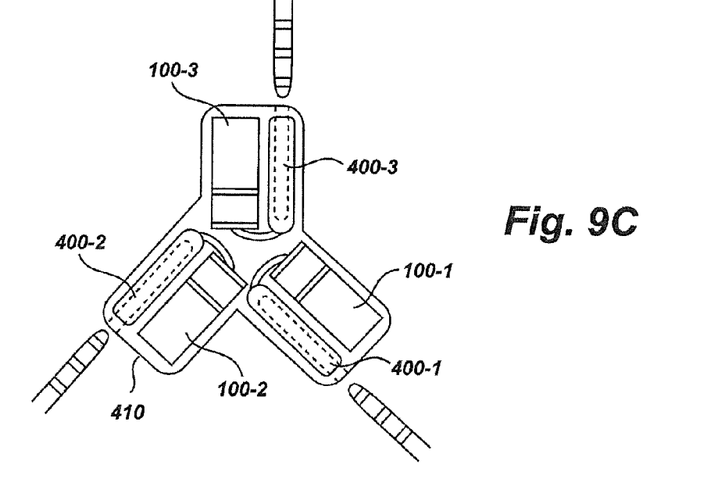
FIG. 9C shows three stimulators and their respective connector assemblies coupled together within an encasing according to principles described herein.

To illustrate, FIGS. 9A-9C are top views of various configurations wherein a plurality of stimulators 100 and their corresponding connector assemblies 400 are coupled one to another by being included within an encasing 410. For example, FIG. 9A illustrates an exemplary configuration where first and second stimulators 100-1 and 100-2 and their corresponding connector assemblies 400-1 and 400-2, respectively, are coupled one to another. Such coupling may be accomplished by encasing both stimulators 100 and their respective connector assemblies 400 within encasing 410. The stimulators 100 and connector assemblies 400 may be coupled one to another in any other way as may serve a particular application.

Likewise, FIG. 9B shows four stimulators 100-1 through 100-4 and their respective connector assemblies 400-1 through 400-4 coupled together within encasing 410. FIG. 9C shows three stimulators (100-1 through 100-3) and their respective connector assemblies (400-1 through 400-3) coupled together within encasing 410.

Figure 10A:
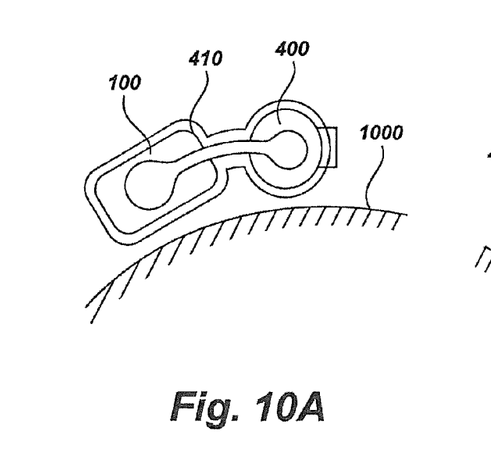
FIGS. 10A-10B show exemplary configurations wherein one or more stimulators are configured to conform to curvatures within a patient according to principles described herein.
Figure 10B:
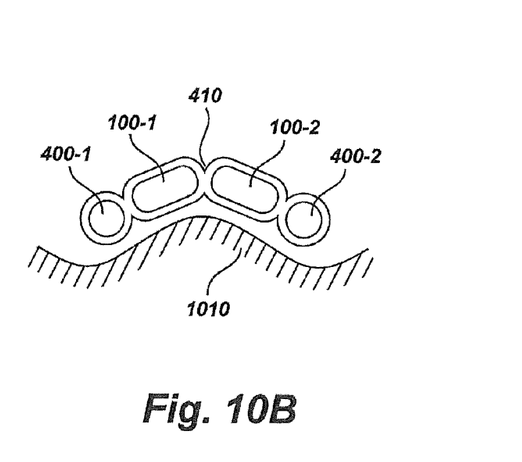

As mentioned, if the encasing 410 and/or the connection in between the stimulator 100 and the connector assembly 400 is flexible, the stimulator 100 may be sutured or otherwise coupled to a non-planar surface within the patient. For example, FIGS. 10A-10B show exemplary configurations wherein the encasing 410 surrounding a one or more stimulator 100 and connector assembly 400 combinations is configured to conform to curvatures within a patient. As shown in FIG. 10A, a single stimulator 100 coupled to a single connector assembly 400 may be encased within a flexible encasing 410 such that the encasing 410 flexes to conform to curvature 1000 within a patient. Likewise, FIG. 10B shows dual stimulators 100-1 and 100-2 and their respective connector assemblies 400-1 and 400-2 encased within an encasing 410 that is configured to conform to another curvature 1010 within a patient.

Figure 11:
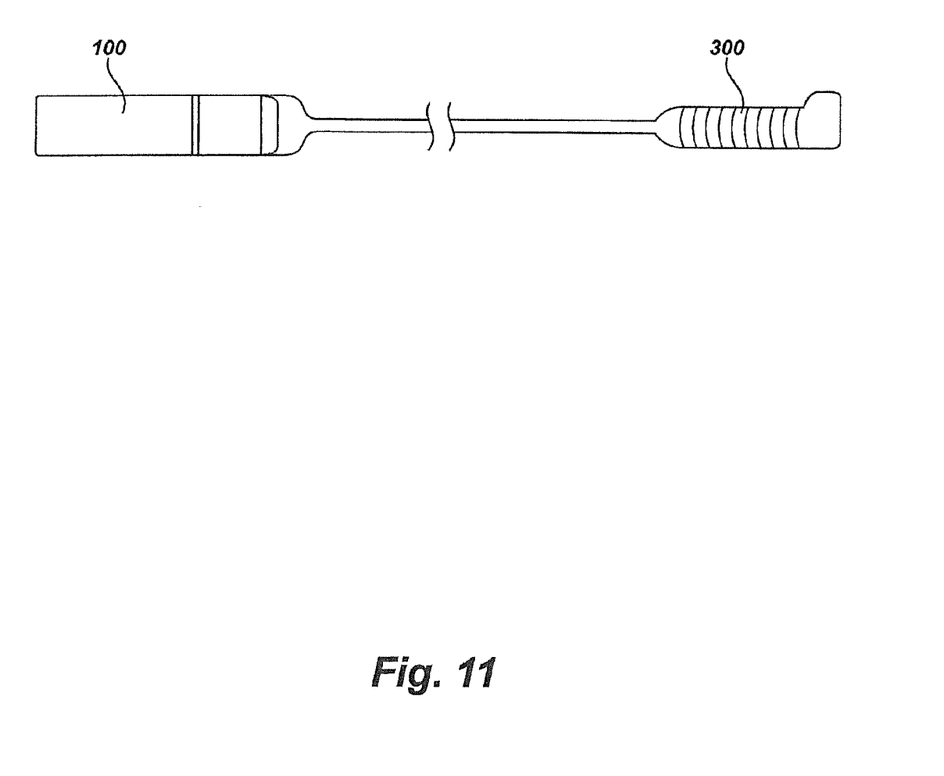
FIG. 11 shows a lead coupled to one of the ends of the stimulator according to principles described herein.

In some alternative examples, the lead 300 may additionally or alternatively be coupled to one of the ends of the stimulator 100, as illustrated in FIG. 11.

The preceding description has been presented only to illustrate and describe embodiments of the invention. It is not intended to be exhaustive or to limit the invention to any precise form disclosed. Many modifications and variations are possible in light of the above teaching.

What is claimed and desired to be protected under United States Letters Patent:

1. A system comprising:
an implantable microstimulator comprising
a single body having a distal end surface, a proximal end surface, and at least one side surface disposed in between the distal and proximal end surfaces,
electrical circuitry disposed within the single body and configured and arranged to generate electrical stimulation current,
a coil disposed within the single body and coupled to the electrical circuitry and configured and arranged to communicate with, or receive power from, an external device, and
a programmable memory unit disposed within the single body and coupled to the electrical circuitry; and
a connector assembly configured to be coupled to the microstimulator and extend parallel to the at least one side surface of the microstimulator;
wherein the connector assembly is further configured to removably receive a portion of a lead and to electrically couple one or more electrodes disposed on the lead to the microstimulator.

2. The system of claim 1, wherein the microstimulator comprises a cylindrical housing defining the body of the microstimulator.

3. The system of claim 1, wherein the microstimulator further comprises at least one electrode disposed on the at least one side surface.

4. The system of claim 1, wherein the connector assembly comprises a lumen open at least one end and extending parallel to the at least one side surface of the microstimulator to receive the portion of the lead; and one or more electrical contacts in communication with the lumen and configured to electrically couple to one or more corresponding electrical contacts disposed on the lead.

5. The system of claim 4, wherein the electrical contacts in communication with the lumen comprise ring contacts.

6. The system of claim 1, further comprising an encasing configured to at least partially surround the microstimulator and the connector assembly.

7. The system of claim 1, further comprising one or more conductive wires configured to electrically couple the electrical circuitry disposed within the microstimulator to the connector assembly.

8. The system of claim 7, further comprising a separate boot member extending from the microstimulator to the connector assembly and at least partially surrounding a portion of the conductive wires.

9. The system of claim 7, wherein a least a portion of the plurality of conductive wires is in a form of a ribbon cable extending from the microstimulator to the connector assembly.

10. The system of claim 1, further comprising a lead having a distal portion, a proximal portion, a plurality of lead electrodes disposed along the distal portion, and a plurality of electrical contacts disposed along the proximal portion and electrically coupled to the plurality of lead electrodes, wherein the connector assembly is configured to removably receive the proximal portion of the lead to facilitate electrical coupling of the lead to the stimulator through the electrical contacts of the lead and to provide electrical stimulation from the microstimulator to one or more stimulation sites within the patient via time lead and the lead electrodes.

11. The system of claim 1, further comprising:
another microstimulator configured to be implanted within a patient, the another microstimulator comprising
a single body having a distal end surface, a proximal end surface, and at least one side surface disposed in between the distal and proximal end surfaces,
electrical circuitry disposed within the single body and configured and arranged to generate electrical stimulation current,
a coil disposed within the single body and coupled to the electrical circuitry and configured and arranged to communicate with or receive power from an external device, and
a programmable memory unit disposed within the single body and coupled to the electrical circuitry;
another connector assembly configured to be coupled to the another microstimulator and extend parallel to the at least one side surface of the another microstimulator; and
an encasing configured to at least partially surround both of the microstimulators and both of the connector assemblies.

12. The system of claim 1, further comprising:
a plurality of other microstimulators configured to be implanted within a patient, each of the other microstimulators comprising
a single body having a distal end surface, a proximal end surface, and at least one side surface disposed in between the distal and proximal end surfaces, electrical circuitry disposed within the single body and configured and arranged to generate electrical stimulation current, a coil disposed within the single body and coupled to the electrical circuitry and configured and arranged to communicate with or receive power from an external device, and a programmable memory unit disposed within the single body and coupled to the electrical circuitry;

a plurality of other connector assemblies configured to be coupled to the plurality of other microstimulators and extend parallel to the at least one side surface of one of the other microstimulators; and a single encasing configured to at least partially surround and hold together all of the microstimulators and all of the connector assemblies.

13. A system comprising:
an implantable microstimulator comprising
a single body having a distal end surface, a proximal end surface, and at least one side surface disposed in between the distal and proximal end surfaces, electrical circuitry disposed within the single body and configured and arranged to generate electrical stimulation current, a rechargeable battery disposed within the single body and coupled to the electrical circuitry, and a coil disposed within the single body and coupled to the rechargeable battery and configured and arranged to receive power from an external device; and a connector assembly configured to be coupled to the microstimulator and extend parallel to the at least one side surface of the microstimulator;

wherein the connector assembly is further configured to removably receive a portion of a lead and to electrically couple one or more electrodes disposed on the lead to the microstimulator.

14. The system of claim 13, further comprising a lead having a distal portion, a proximal portion, a plurality of lead electrodes disposed along the distal portion, and a plurality of electrical contacts disposed along the proximal portion and electrically coupled to the plurality of lead electrodes, wherein the connector assembly is configured to removably receive the proximal portion of the lead to facilitate electrical coupling of the lead to the stimulator through the electrical contacts of the lead and to provide electrical stimulation from the microstimulator to one or more stimulation sites within the patient via the lead and the lead electrodes.

15. A system comprising:
an implantable microstimulator comprising
a single body having a distal end surface, a proximal end surface, and at least one side surface disposed in between the distal and proximal end surfaces, electrical circuitry disposed within the single body and configured and arranged to generate electrical stimulation current, a coil disposed within the single body and coupled to the electrical circuitry and configured and arranged to communicate with an external device, and a programmable memory unit disposed within the single body and coupled to the electrical circuitry and the coil, wherein the programmable memory unit is configured and arranged for adjustment of one or more stimulation parameters stored on the programmable memory unit by communication using the coil; and a connector assembly configured to be coupled to the microstimulator and extend parallel to the at least one side surface of the microstimulator;

wherein the connector assembly is further configured to removably receive a portion of a lead and to electrically couple one or more electrodes disposed on the lead to the microstimulator.

16. The system of claim 15, further comprising a lead having a distal portion, a proximal portion, a plurality of lead electrodes disposed along the distal portion, and a plurality of electrical contacts disposed along the proximal portion and electrically coupled to the plurality of lead electrodes, wherein the connector assembly is configured to removably receive the proximal portion of the lead to facilitate electrical coupling of the lead to the stimulator through the electrical contacts of the lead and to provide electrical stimulation from the microstimulator to one or more stimulation sites within the patient via the lead and the lead electrodes.

17. The system of claim 15, wherein the connector assembly comprises a lumen open at least one end and extending parallel to the at least one side surface of the microstimulator to receive the portion of the lead; and one or more electrical contacts in communication with the lumen and configured to electrically couple to one or more corresponding electrical contacts disposed on the lead.

18. A method of stimulating patient tissue, the method comprising:
implanting the system of claim 1;
removably coupling a lead having one or more electrodes disposed thereon to the connector assembly of the system;
generating electrical stimulation with the microstimulator of the system; and
applying the electrical stimulation to one or more stimulation sites within a patient via the one or more electrodes of the lead.

19. A method of stimulating patient tissue, the method comprising:
implanting the system of claim 13;
removably coupling a lead having one or more electrodes disposed thereon to the connector assembly of the system;
generating electrical stimulation with the microstimulator of the system; and
applying the electrical stimulation to one or more stimulation sites within a patient via the one or more electrodes of the lead.

20. A method of stimulating patient tissue, the method comprising:
implanting the system of claim 15;
removably coupling a lead having one or more electrodes disposed thereon to the connector assembly of the system;
generating electrical stimulation with the microstimulator of the system; and
applying the electrical stimulation to one or more stimulation sites within a patient via the one or more electrodes of the lead.

* * * * *